US009339208B2

(12) United States Patent
Wood et al.

(10) Patent No.: US 9,339,208 B2
(45) Date of Patent: May 17, 2016

(54) TRACHEAL TUBE WITH PRESSURE MONITORING LUMEN AND METHOD FOR USING THE SAME

(75) Inventors: Lockett E. Wood, Lyons, CO (US); Sarah Hayman, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 1132 days.

(21) Appl. No.: 12/689,049

(22) Filed: Jan. 18, 2010

(65) Prior Publication Data
US 2011/0178419 A1 Jul. 21, 2011

(51) Int. Cl.
A61B 5/08 (2006.01)
A61M 16/04 (2006.01)
A61M 16/00 (2006.01)

(52) U.S. Cl.
CPC .................. *A61B 5/08* (2013.01); *A61M 16/04* (2013.01); *A61M 16/0459* (2014.02); *A61M 16/0484* (2014.02); *A61B 2562/0247* (2013.01); *A61M 16/0434* (2013.01); *A61M 2016/0027* (2013.01)

(58) Field of Classification Search
CPC .... A61B 5/08; A61M 16/04; A61M 16/0484; A61M 2016/0027
USPC ................. 600/538–542; 128/204.18–205.26
See application file for complete search history.

(56) References Cited

U.S. PATENT DOCUMENTS

| 3,931,822 A | 1/1976 | Marici |
| 4,285,340 A | 8/1981 | Gezari et al. |
| 4,305,392 A | 12/1981 | Chester |
| 4,344,436 A | 8/1982 | Kubota |
| 4,488,548 A | 12/1984 | Agdanowski |
| 4,526,196 A | 7/1985 | Pistillo |
| 4,552,558 A | 11/1985 | Muto |
| 4,565,194 A | 1/1986 | Weerda et al. |
| 4,584,998 A | 4/1986 | McGrail |
| 4,630,606 A | 12/1986 | Weerda et al. |
| 4,840,173 A | 6/1989 | Porter |
| 4,898,168 A | 2/1990 | Yule |

(Continued)

FOREIGN PATENT DOCUMENTS

WO 9422518 10/1994
WO WO 2009129506 A1 * 10/2009 ............ A61M 16/00

OTHER PUBLICATIONS

Hess, Dean. "Ventilator Waveforms and the Physiology of Pressure Support Ventilation." Respiratory Care, vol. 50, No. 2. Feb. 2005. pp. 166-186.*

(Continued)

*Primary Examiner* — Navin Natnithithadha
*Assistant Examiner* — Meredith Weare
(74) *Attorney, Agent, or Firm* — Fletcher Yoder PC

(57) ABSTRACT

According to various embodiments, methods and systems for determining pressure in the lungs may employ tracheal pressure measurements. The tracheal pressure measurements may be obtained through a pressure monitoring lumen associated with a tracheal tube. Such systems may include a purging or flushing mechanism to keep the pressure monitoring lumen free of any obstructions. The flushing mechanism may utilize fluids delivered through the pressure monitoring lumen at a predetermined point in the breathing cycle and/or at a predetermined pressure relative to the respiratory gases. The resulting pressure measurements may be used to determine a more accurate estimate of lung pressure, which in turn may be used to control a ventilator and provide breathing assistance to a patient.

6 Claims, 9 Drawing Sheets

(56) References Cited

U.S. PATENT DOCUMENTS

| | | | |
|---|---|---|---|
| 5,218,970 A | | 6/1993 | Turnbull et al. |
| 5,235,973 A | | 8/1993 | Levinson |
| 5,285,778 A | | 2/1994 | Mackin |
| 5,361,753 A | | 11/1994 | Pothmann et al. |
| 5,431,637 A | | 7/1995 | Okada et al. |
| 5,546,935 A | | 8/1996 | Champeau |
| 5,591,130 A | | 1/1997 | Denton |
| 5,676,635 A | | 10/1997 | Levin |
| 5,740,796 A | | 4/1998 | Skog |
| 5,752,921 A | | 5/1998 | Orr |
| 5,819,723 A | | 10/1998 | Joseph |
| 5,885,248 A | | 3/1999 | Denton |
| 5,906,204 A | | 5/1999 | Beran et al. |
| 6,062,223 A | | 5/2000 | Palazzo et al. |
| 6,298,848 B1 | * | 10/2001 | Skog ................. 128/204.18 |
| 6,315,739 B1 | * | 11/2001 | Merilainen et al. ........... 600/587 |
| 6,450,164 B1 | * | 9/2002 | Banner et al. ............ 128/204.21 |
| 6,474,333 B1 | * | 11/2002 | Heinonen ................ 128/203.12 |
| 6,530,898 B1 | | 3/2003 | Nimkar et al. |
| 6,647,984 B1 | | 11/2003 | O'Dea |
| 6,659,962 B2 | * | 12/2003 | Ricciardelli ................. 600/538 |
| 6,820,618 B2 | | 11/2004 | Banner et al. |
| 6,918,391 B1 | | 7/2005 | Moore |
| 7,051,736 B2 | | 5/2006 | Banner et al. |
| 7,052,456 B2 | | 5/2006 | Simon |
| 7,089,942 B1 | | 8/2006 | Grey |
| 7,152,603 B1 | | 12/2006 | Crump et al. |
| 7,191,782 B2 | | 3/2007 | Madsen |
| 7,503,328 B2 | | 3/2009 | Kolobow et al. |
| 2005/0279360 A1 | | 12/2005 | Wei |
| 2007/0044807 A1 | | 3/2007 | Madsen et al. |
| 2008/0110468 A1 | | 5/2008 | Nelson et al. |
| 2008/0210235 A1 | | 9/2008 | Field et al. |
| 2008/0257353 A1 | | 10/2008 | Yamamoto et al. |
| 2009/0038620 A1 | | 2/2009 | Efrati |
| 2010/0051026 A1 | * | 3/2010 | Graboi .................... 128/203.12 |
| 2010/0326446 A1 | * | 12/2010 | Behlmaier ................ 128/207.15 |
| 2011/0144514 A1 | * | 6/2011 | Booker ........................ 600/529 |
| 2011/0197885 A1 | * | 8/2011 | Wondka et al. .......... 128/204.22 |
| 2011/0259327 A1 | * | 10/2011 | Wondka et al. .......... 128/203.14 |

OTHER PUBLICATIONS

Lomholt, N., A Device for Measuring the Lateral Wall Cuff Pressure of Endotracheal Tubes, Acta Anaesthesiologica Scandinavica, Dec. 1992, pp. 775-778, Issue 36.

Pollard, Richard. J. MD et al., Endotracheal Tube Location Verified Reliably by Cuff Palpation, Anesthesia and Analgesia, 1995, pp. 135-138.

Cardoso, Monica M. S. C. MD et al., Portable Devices Used to Detect Endotracheal Intubation During Emergency Situations: A Review, Critical Care Medicine, May 1998, pp. 957-964, vol. 26, Issue 5.

Guttmann, Josef PhD et al., Continuous Calculation of Intratracheal Pressure in the Presence of Pediatric Endotracheal Tubes, Critical Care Medicine, Apr. 2000, pp. 1-21, vol. 28, Issue 4.

Karasawa, Fujio. MD et al., Profile Soft-Seal Cuff, a New Endotracheal Tube, Effectively Inhibits an Increase in the Cuff Pressure through High Compliance Rather than Low Diffusion of Nitrous Oxide, Anesthesia and Analgesia, Dec. 2001, pp. 140-144, Issue 92.

Sondergaard, Soren. et al., Direct Measurement of Intratracheal Pressure in Pediatric Respiratory Monitoring, Pediatric Research, Dec. 2002, vol. 51, No. 3.

Dullenkopf, A. et al., Air Leakage Around Endotracheal Tube Cuffs, European Journal of Anaesthesiology, Dec. 2004, pp. 448-453, Issue 21.

Kolobow, Theodor et al., The Mucus Slurper: A Novel Tracheal Tube that Requires no Tracheal Tube Suctioning. A Preliminary Report, Journal of Intensive Care Medicine, Jan. 2006, pp. 1414-1418, Issue 32.

Coated Endotracheal Tube and Mucus Shaver to Prevent Hospital-Aquired Infections, http://clinicaltrials.gov/ct2/show/NCT00341354, ClinicalTrials.gov, 2006, pp. 1-3.

O'Neal PhD, et al., Subglottic Secretion Viscosity and Evacuation Efficiency, Biological Research for Nursing, http://brn.sagepub.com, Jan. 2007, pp. 202-209, vol. 8, No. 3.

Aspiration of Subglottic Secretions using Hi-Lo Evac Endotracheal Tube: Tube Size and Incidence of Suction Lumen Dysfunction, http://clinicaltrials.gov/ct2/show/NCT00450476, ClinicalTrials.gov, 2007, pp. 1-3.

Lorente, Leonardo et al., Influence of an Endotracheal Tube with Polyurethane Cuff and Subglottic Secretion Drainage on Pneumonia, American Journal of Respiratory and Critical Care Medicine, May 2007, pp. 1079-1083, vol. 176.

Bassi, Gianlugig Li MD et al., A 72-hour Study to Test the Efficacy and Safety of the "Mucus Slurper" in Mechanically Ventilated Sheep, Critical Care Medicine, 2007, pp. 209-911, vol. 35, No. 3.

Removal of Endotracheal Tube Secreations Comprehensively Until Extubation (RESCUE), http://clinicaltrials.gov/ct2/show/NCT00663637, ClinicalTrials.gov, 2008, pp. 1-3.

Horisberger, T. et al., Measurement of Tracheal Wall Pressure: A Comparison of Three Different in Vitro Techniques, Journal of the Association of Anaesthetists of Great Britain and Ireland, Dec. 2008, pp. 418-422, Issue 63.

Khazin, Vadim MD et al., Gastroesophageal Regurgitation during Anesthesia and Controlled Ventilation with Six Airway Devices, Journal of Clinical Anesthesia, Dec. 2008, pp. 508-513, Issue 20.

Orr, Joseph A., Tracheal Pressure Controller for Ventilators, National Institute of Allergy and Infectious Diseases, Jun. 2010, pp. 1-7.

Teleflex ISIS HVT, Cuffed Endotracheal Tubes, Hudson RCI-Products, 2010, pp. 1-5.

Sheridan ETCO2 Uncuffed Endotracheal Tubes, Monitoring Lumen Tubes, Hudson RCI, 2010, pp. 1-2.

* cited by examiner

TRACHEAL TUBE WITH PRESSURE MONITORING LUMEN AND METHOD FOR USING THE SAME

BACKGROUND

The present disclosure relates generally to medical devices and, more particularly, to airway devices, such as tracheal tubes.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea and into the lungs, for example during patient ventilation. Such tracheal tubes may include endotracheal (ET) tubes, tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

To seal these types of tracheal tubes, an inflatable cuff may be associated with the tubes. When inflated, the cuff generally expands into the surrounding trachea to seal the tracheal passage around the tube to facilitate the controlled delivery of gases via a medical device (e.g., through the tube). For intubated patients, the flow rate and volume of gas transferred into the lungs, which may vary according to the condition of each patient, may be controlled by the settings of a ventilator. One factor that is used to determine the ventilator settings may be an airway pressure measurement, which is typically obtaining by measuring the pressure along the breathing circuit (e.g., medical tubing connecting the tracheal tube to the ventilator) at a point outside the patient. Airway pressure measured in the breathing circuit at a point outside the patient may be a useful surrogate for the pressure in the lungs, which may in turn be used for calculating a number of ventilator settings, for example settings involving pressure limits.

However, in circumstances where the internal diameter of the tracheal tube is diminished, for example through the buildup of mucosal secretions that may partially block the airflow passage of the tracheal tube, the lung pressure may differ from the airway pressure measurement taken outside the patient. Accordingly, an airway pressure measurement may not always serve as a reliable substitute for lung pressure measurements.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

Figure 1:
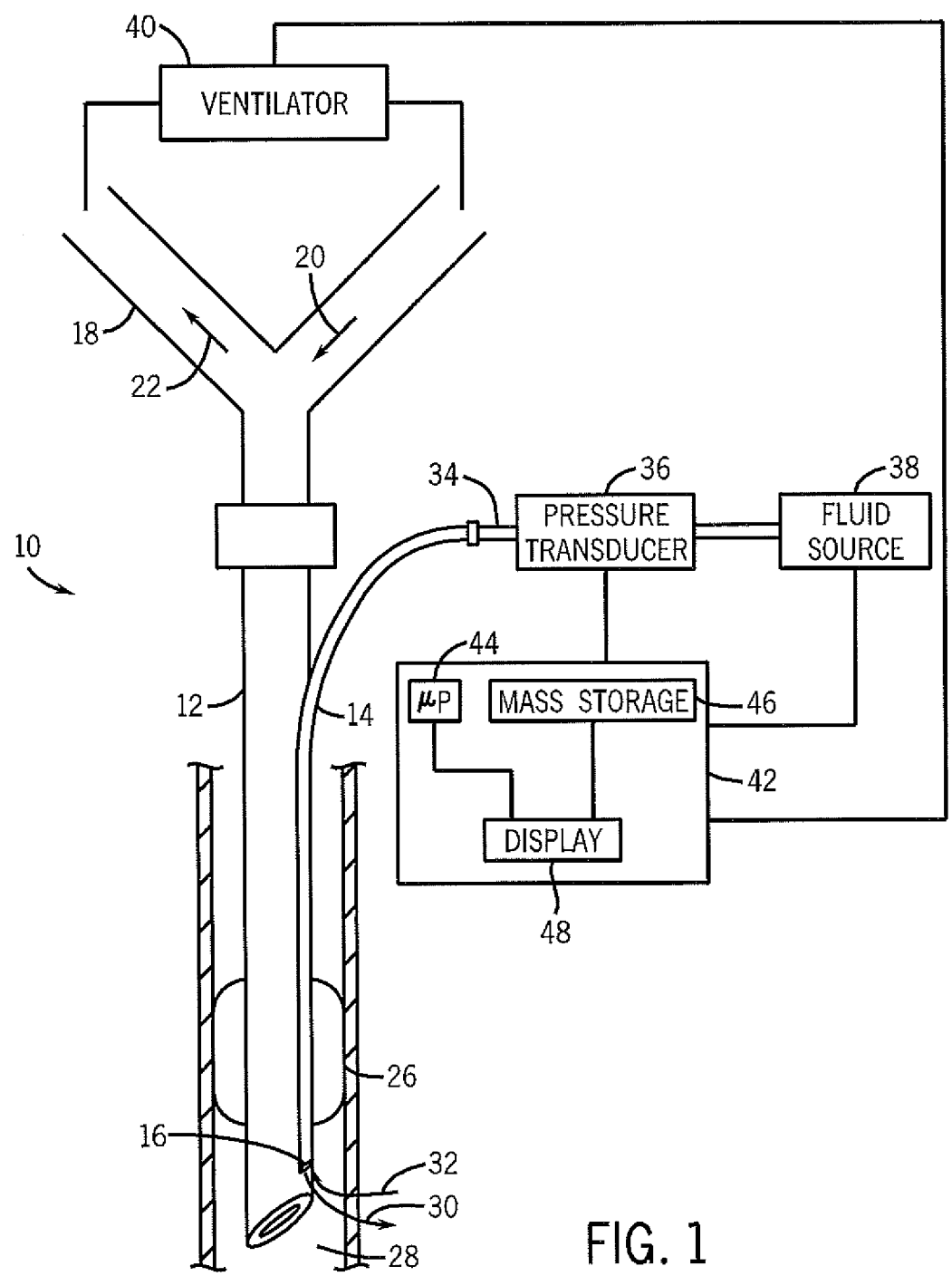
FIG. 1 illustrates a system including an endotracheal tube with a pressure monitoring lumen according to embodiments of the present techniques.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Because direct measurements of the pressure in the internal space of the lungs is difficult, clinicians and respiratory specialists may use surrogate measurements of pressure along various points of breathing circuit or the patient airway to estimate the lung pressure. The lung pressure estimates may then be used to determine the efficacy of the ventilation (e.g., the dynamic intrapulmonary compliance) and, in some cases, may be used to control the settings of a ventilator, either manually or automatically, to provide a clinical benefit to the patient.

Airway pressure may be estimated by using measurements of pressure taken along various points of the breathing circuit that are proximal to the tracheal tube. For example, such measurements may be used to assess a patient work of breathing, which may include the airway resistance during movement of air into and out of the lungs. If the work of breathing of the patient increases, clinicians may assess whether the increase is due to increased airway resistance in the patient (e.g., stiffened lung tissue, which may be related to a clinical condition) or increased resistance in the tracheal tube due to buildup of biofilms on the inner diameter of the tube. Because airway pressure measurements taken proximal to the tracheal tube may not provide information about resistance built up distally, either in the patient or in the tube, trachea pressure measurements may provide information to the clinician about airway or tube-originated resistance. Trachea pressure may refer to pressure in the airway space below the cuff and/or near the distal tip of the tracheal tube.

In particular, because the internal diameter of tracheal tube may change during the time that the patient is intubated (e.g., a buildup of patient secretions within the tube may change the inner diameter), measurements taken upstream of the tracheal tube in the breathing circuit may not be reliable for estimating pressure in the lungs. In certain embodiments, a measurement of tracheal pressure may be used as a surrogate for lung pressure or other pulmonary pressure measurements. The tracheal space is contiguous with the lung space, and tracheal pressure may be a more reliable measurement than measurements taken far upstream along the breathing circuit. Trachea pressure may be determined by using pressure transducers inserted at the distal end of the endotracheal tube or by sampling the gas in the tracheal space with a lumen connected to a proximally located pressure transducer. However, during long-term patient monitoring, the distal end of the tracheal tube may become covered in mucus or secretions, which may interfere with a pressure transducer located at the distal end of the tube or which may block a pressure monitoring lumen. For example, when a patient coughs, mucus from the lungs may be deposited at the distal end of the tracheal tube. When the pressure transducer or pressure monitoring lumen is covered in mucus, measurement accuracy may be affected.

Accordingly, the disclosed embodiments provide a more accurate method and system for determining trachea pressure by providing a tracheal tube with a pressure monitoring lumen that samples gas at or near the distal end of the tracheal tube. The pressure monitoring lumen may be kept clear of mucus blockage through flushing of the lumen with a fluid, such as a gas. By timing the flushing of the pressure monitoring lumen with a patient mechanical breathing cycle, the flushing may occur at a time of increased effectiveness with a minimum change in the total volume of fluid added to the lungs. For example, when the flushing occurs at a time in the breathing cycle associated with a minimum pressure in the lungs, such as at the end of exhalation, the pressure of the purging fluid in the lumen may easily overcome the lung and trachea pressure so that any blockage in the lumen may be cleared away. In contrast, when the pressure in the trachea is higher than the purging pressure, the purging pressure may not overcome the outside pressure in the trachea, which may limit the effectiveness of the purging fluid. In other embodiments, the purging pressure may be controlled such that the purging pressure is higher than the pressure of respiratory gases being delivered to the lungs over the course of one or more breathing cycles. In one such embodiment, the purging pressure may be a certain offset from the airway pressure (i.e., the difference between the airway pressure and the purging pressure may be substantially constant) so that the effect of the flushing gas on pressure measurements may be subtracted or, in embodiments in which the difference is relatively small, ignored.

In certain presently contemplated embodiments, the trachea pressure may be used to evaluate, adjust, or correct airway pressure values obtained along the breathing circuit or ventilator settings. For example, if the estimate of trachea pressure varies significantly from the airway pressure measured upstream at a point closer to the ventilator, a clinician may be able to determine that the tracheal tube is blocked with secretions or other buildup, or that some other condition has developed, which may involve action by the clinician. In addition, if the pressure in the pressure monitoring lumen is unexpectedly high, such measurements may be indicative of a blockage in the lumen. Such information may be used to deliver more purging fluid through the lumen and/or to provide an indication to a caregiver of the potential blockage.

In certain embodiments, the disclosed tracheal tubes, systems, and methods may be used in conjunction with any appropriate medical device, including a feeding tube, an endotracheal tube, a tracheotomy tube, a circuit, an airway accessory, a connector, an adapter, a filter, a humidifier, a nebulizer, nasal cannula, or a supraglottal mask/tube. The present techniques may also be used to monitor any patient benefiting from mechanical ventilation, e.g., positive pressure ventilation. Further, the devices and techniques provided herein may be used to monitor a human patient, such as a trauma victim, an intubated patient, a patient with a tracheotomy, an anesthetized patient, a cardiac arrest victim, a patient suffering from airway obstruction, or a patient suffering from respiratory failure.

FIG. 1 shows an exemplary tracheal tube system 10 that has been inserted into the trachea of a patient. The system 10 includes a tracheal tube 12, shown here as an endotracheal tube, with a pressure monitoring lumen 14 that may be incorporated into the walls of the tracheal tube, e.g., the lumen 14 may be coextruded in the walls. The pressure monitoring lumen 14 may terminate in an opening 16 that formed in the walls of the tracheal tube 12 to allow the pressure monitoring lumen to be in fluid communication with the patient airway.

The system 10 may also include a respiratory circuit connected to the endotracheal tube 12 that allows one-way flow of expired gases away from the patient and one-way flow of inspired gases towards the patient. For example, the system 10 may include a Y-connector 18 in fluid communication with a source of respiratory gas. The Y-connector may include a branch for airflow into the lungs (i.e., inspiration), represented by arrow 20 and airflow out of the lungs (i.e., exhalation), represented by arrow 22. The system 10 may include any number of other connectors or medical tubing to provide respiratory gases from a gas source to the lungs. The respiratory circuit, including the tube 12, may include standard medical tubing made from suitable materials such as polyurethane, polyvinyl chloride (PVC), polyethylene teraphthalate (PETP), low-density polyethylene (LDPE), polypropylene, silicone, neoprene, polytetrafluoroethylene (PTFE), or polyisoprene.

The tracheal tube 12 may also be associated with an inflatable cuff 26 that functions to form a seal against the tracheal walls and isolate the lower airway space 28 of the lower trachea and lungs during mechanical ventilation. The pressure monitoring lumen 14 is configured to sample air from the lower airway space 28. The system 10 also includes a mechanism for maintaining flow through the pressure monitoring lumen 14 so that blockages do not form around the opening 16. As such, the pressure monitoring lumen 14 has either continuous or sporadic airflow out of the opening 16, represented by arrow 30, and may also receive airflow into the lumen, represented by arrow 32. Given that the airflow to the lumen is bidirectional, the pressure in the lumen 14 may represent an equilibrated pressure from the inflow and outflow components.

The pressure monitoring lumen 14 is in fluid communication with a pressure transducer 36 and a fluid source 38, that are, for example, connected by a conduit 34. It should be understood that conduit 34 may include any number of additional conduits and couplers. As shown, the pressure transducer 36 may be on or within conduit 34, which in turn may be in fluid communication with pressure monitoring lumen 14. In other embodiments, the pressure transducer 36 may be a part of coupler that connects conduit 34 to pressure monitoring lumen 14. In other embodiments, the pressure transducer 36 may be part of a proximal portion of pressure monitoring lumen 14.

The system 10 may also include devices that facilitate positive pressure ventilation of a patient, such as the ventilator 40, which may include any suitable device or system, such as those available from Nellcor Puritan Bennett LLC. The system may also include a monitor 42 that may be configured to implement embodiments of the present disclosure to determine pressures based upon the pressure detected by the pressure transducer 36. It should be understood that the monitor 42 may be a stand-alone device or may, in certain embodiments, be integrated into a single device with, for example, the ventilator 40.

The monitor 42 may include processing circuitry, such as a microprocessor 44 coupled to an internal bus and a display 48. In certain embodiments, the system 10 may also provide calibration information for the purging mechanism and/or pressure transducer 36. The information may then be stored in mass storage device 46, such as RAM, PROM, optical storage devices, flash memory devices, hardware storage devices, magnetic storage devices, or any suitable computer-readable storage medium. The information may be accessed and operated upon according to instructions executed by a microprocessor 44, or any suitable processing circuitry. In certain embodiments, the information may be used in calculations for estimating of pressure in the lungs. The monitor 42 may be configured to provide indications of the lung pressure, such as an audio, visual or other indication, or may be configured to communicate the estimated lung pressure to another device, such as the ventilator 40.

Figure 2:
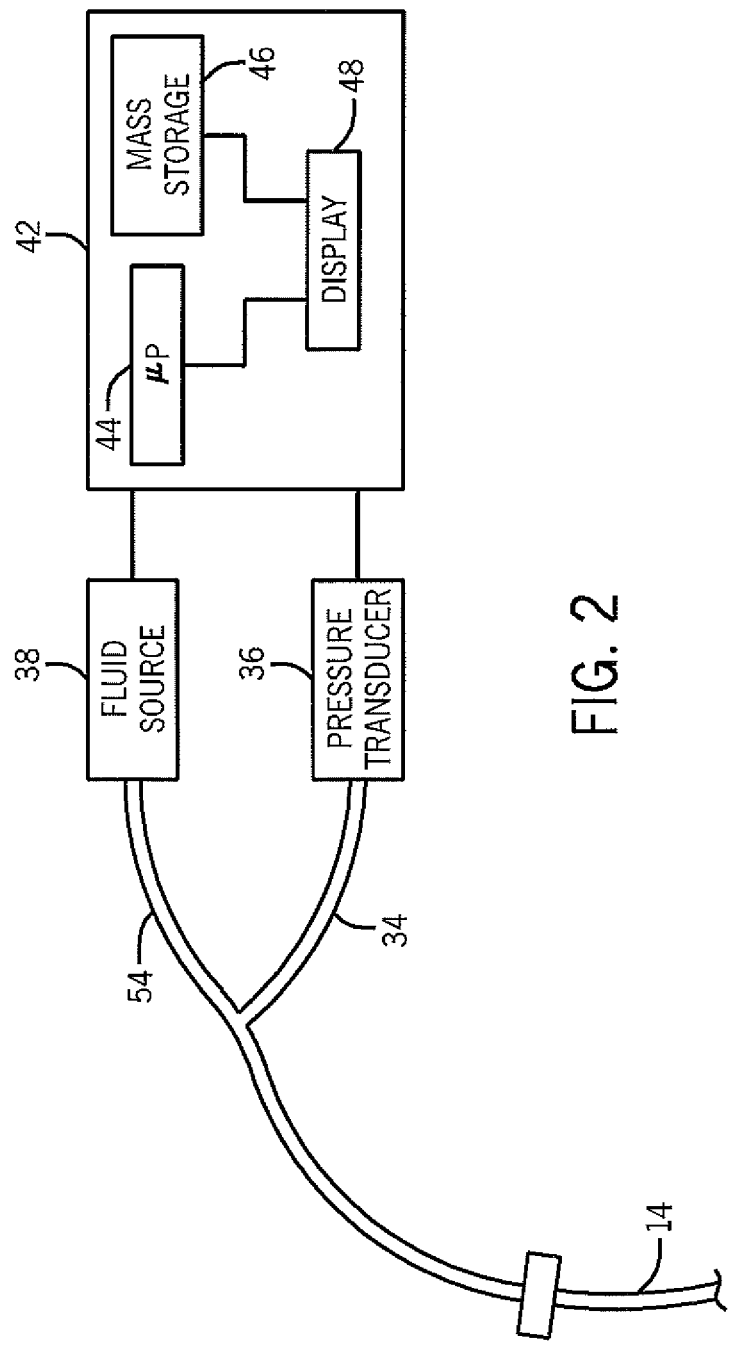
FIG. 2 is a block diagram of an example of a pressure monitoring lumen purging system that may be used in conjunction with the system of FIG. 1.

FIG. 2 is block diagram of certain fluid purging components. In particular embodiments, the purging system may include a fluid source 38 and a pressure transducer 36 that are in fluid communication with the pressure monitoring lumen 14. In FIG. 2, these components are shown as being in parallel, i.e., the fluid source may be on a separate line or on a separate branch of conduit 34 so long as fluids from the fluid source 38 are able to be transferred to the pressure monitoring lumen 14. In other embodiments, these components may be in-line along the conduit 34. The purging components may be provided as a kit or unit, which may also include a coupler that is configured to connect the components to the pressure monitoring lumen 14 and any electrical connections to the monitor 42 or other medical device. In certain presently contemplated embodiments, the pressure transducer 36 may be located at the proximal end of the pressure monitoring lumen 14 or within a connection point or another connecting conduit in fluid communication with the pressure monitoring lumen 14. In addition, the fluid source 38 may be a central fluid source, e.g., a hospital source, and the purging system may include a coupler or mechanism for connecting the central fluid source to the pressure monitoring lumen 14 and regulating the pressure to appropriate purging pressure.

Figure 3:
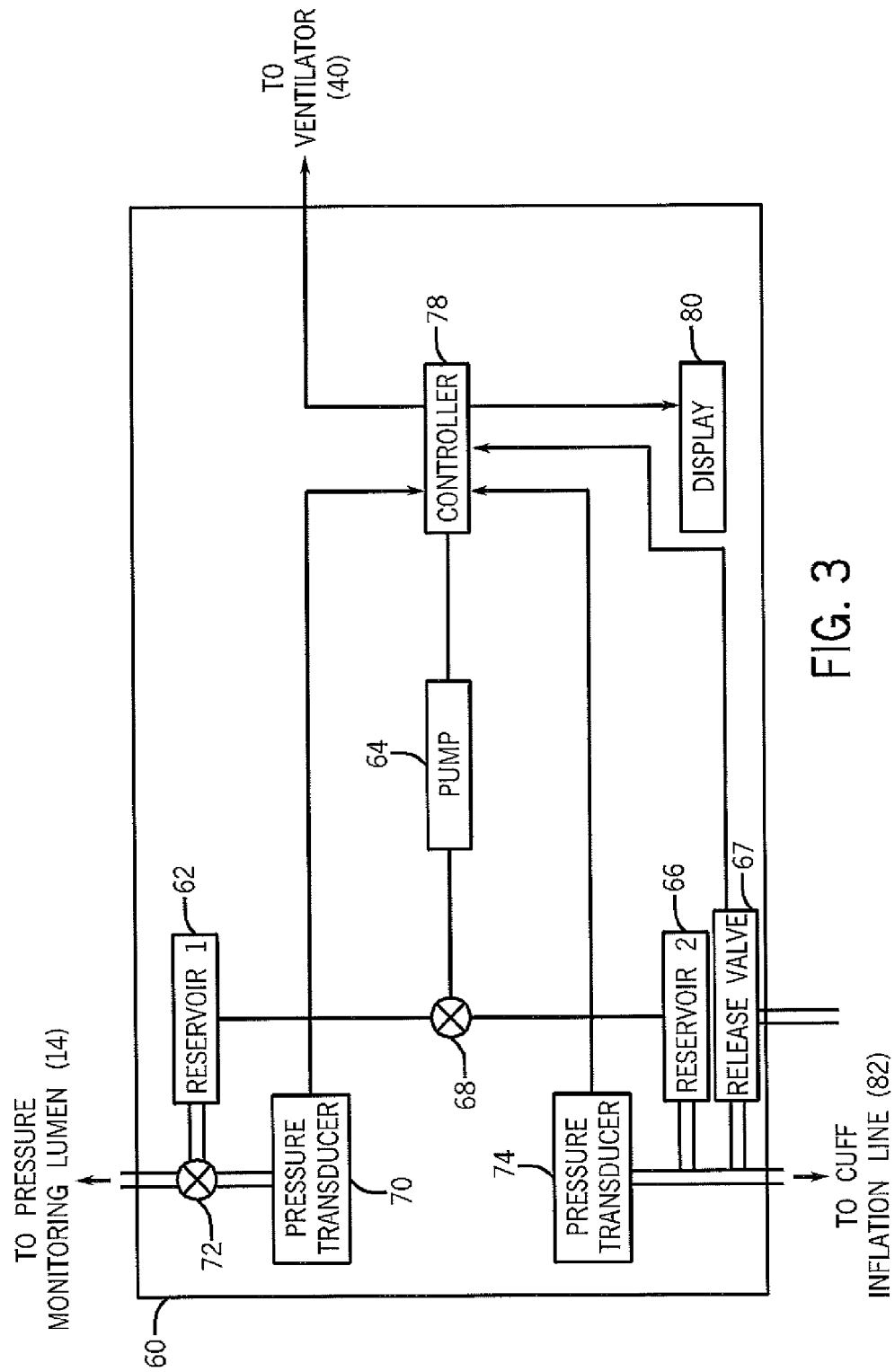
FIG. 3 is a block diagram of an additional example of a pressure monitoring lumen purging system that may be used in conjunction with the system of FIG. 1.

The purging components may be housed in a unitary device, such as purging system 60, shown in FIG. 3, that provides additional functionality to the system 10. For example, purging system 60 may include a first fluid reservoir 62 (i.e., fluid source) configured to provide outflow to a pressure monitoring lumen and a second fluid reservoir 66 configured to provide outflow for inflating the cuff 26. The first fluid reservoir 62 may be a low compliance reservoir (i.e., relatively rigid), while the second fluid reservoir 66 may be a high compliance reservoir (i.e., relatively flexible). These two fluid sources may be interconnected by a pump 64 and a three-way valve 68. The three-way valve may allow reservoir 62 and reservoir 66 to be filled in turn when their fluid levels have been depleted. Alternatively, the system 60 may include an outside fluid source rather than a motive force for directing fluid to reservoir 62 and reservoir 66. Reservoir 62 may be in fluid communication with pressure monitoring lumen 14 via three-way valve 72, which may allow air to flow from the reservoir 62 into the lumen 14. When the valve is actuated, air from the pressure monitoring lumen 14 may flow into fluid communication with a pressure transducer 70 for obtaining trachea pressure measurements. Such an arrangement may allow pressure measurements to take place when there is no purging fluid being delivered to pressure monitoring lumen 14. To control the timing of the trachea pressure measurements and the timing and pressure of the purging fluid, the reservoir 62, three-way valve 72, and pressure transducer 70 may be in communication with a central controller 78.

In addition, the system 60 may provide inflation control for the inflatable cuff 26 by diverting a portion of the pumped fluid to the second reservoir 66. A pressure transducer 74 in fluid communication with a cuff inflation line 82 may allow the central controller 78 to determine when inflation of the cuff 26 is necessary. Generally, it is envisioned that the main outflow of fluids from system 60 will be directed into the pressure monitoring lumen 14, and that the inflation of the cuff 26 will occur intermittently when the cuff pressure drops below a certain threshold. However, because fluids may accumulate in separate reservoirs 62 and 66, fluid outflow may occur to both the pressure monitoring lumen 14 and the cuff inflation line 82 simultaneously. Controller 78 may control the replenishment of fluid to reservoirs 62 and 66. Further, the system 60 may include pressure regulators for controlling the pressure from the first reservoir 62 into the pressure monitoring lumen 14 and from the second reservoir 66 into the cuff inflation line 82. The system 60 may also include a controlled pressure relief valve 67 to relieve pressure in the cuff 26, for example in cases where the cuff 26 becomes inflated above a desired pressure. The pressure relief valve 67 may be under control of the central controller 78, which may provide instructions for pressure relief based on information from the pressure transducer 74 associated with the cuff inflation line 82. The system 60 may also include a display 80 for displaying indications of pressure in the pressure monitoring lumen and/or the cuff inflation line 82. In addition, the display 80 may also display indications of whether purging pressure and/or cuff inflation pressure is being applied. To coordinate timing of the purging pressure to the pressure monitoring lumen 14 to the breathing cycle, the controller 80 may also be configured to communicate with ventilator 40.

Figure 4:
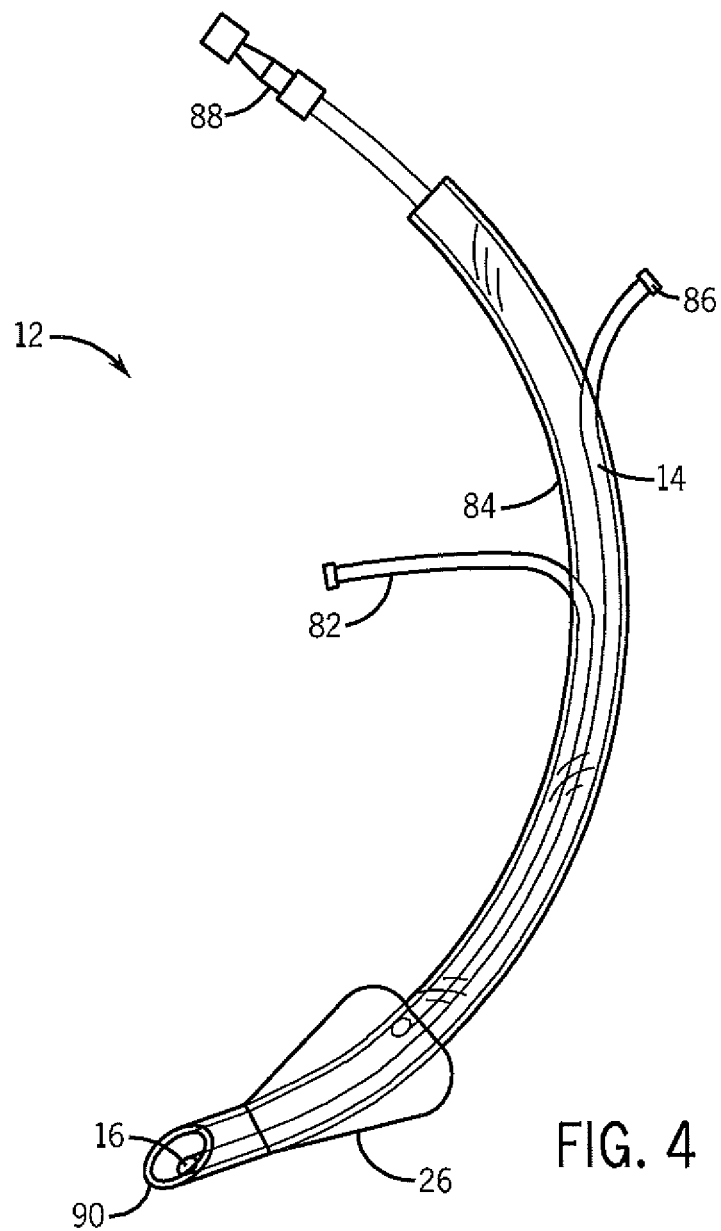
FIG. 4 is a perspective view of an endotracheal tube with a pressure monitoring lumen that may be used in conjunction with the system of FIG. 1.

FIG. 4 is a perspective view of an exemplary tracheal tube 12 according to certain presently contemplated embodiments. The tracheal tube 12 includes a pressure monitoring lumen 14 that may be formed (e.g., through extrusion) in the tracheal walls 62. At a distal end, the lumen 14 terminates in an opening 16 that is distal to the cuff 26. At a proximal end, the lumen 14 may, in certain embodiments, terminate in a suitable coupler 86. As shown in FIG. 4, the opening 16 may be located on a slant portion of a distal end 64 of the tube 12. For example, the opening 16 may be formed by cutting a distal end of the tube and revealing the opening. In other embodiments, any opening at the slanted distal end 90 may be heat sealed and an opening 16 may be formed by puncturing or otherwise forming a hole in the tracheal tube walls 84 to access the lumen 14. The pressure monitoring lumen 14 may terminate in any suitable connector, such as connector 88, to facilitate fluid communication with the pressure transducer 36.

The tube 12 may include a cuff 26 that may be inflated via a separate inflation lumen 82. In addition, the tube 12 may include a calibration element, such as connector 88, that may be suitably configured to connect to a receiving port on the monitor 42. The connector 88 may contain an information element, such as a memory circuit (e.g., an EPROM, EEPROM, coded resistor, or flash memory device) for storing calibration information for the pressure monitoring lumen 14 (e.g., a resistance of the lumen 14) and/or the pressure transducer 36. Alternatively, the pressure transducer 36 may include a passive or active RFID circuit that may be read wirelessly to convey pressure monitoring information and calibration information to the monitor 42. In other embodiments, tube identifying data, calibration data, and so forth may simply be entered manually.

The tube 12, the lumen 14, and the cuff 26 are formed from materials having suitable mechanical properties (such as puncture resistance, pin hole resistance, tensile strength), chemical properties (such as biocompatibility). In one embodiment, the walls of the cuff 26 are made of a polyurethane having suitable mechanical and chemical properties. An example of a suitable polyurethane is Dow Pellethane® 2363-80A. In another embodiment, the walls of the cuff 26 are made of a suitable polyvinyl chloride (PVC). In certain embodiments, the cuff 26 may be generally sized and shaped as a high volume, low pressure cuff that may be designed to be inflated to pressures between about 15 cm $H_2O$ and 30 cm $H_2O$.

Figure 5:
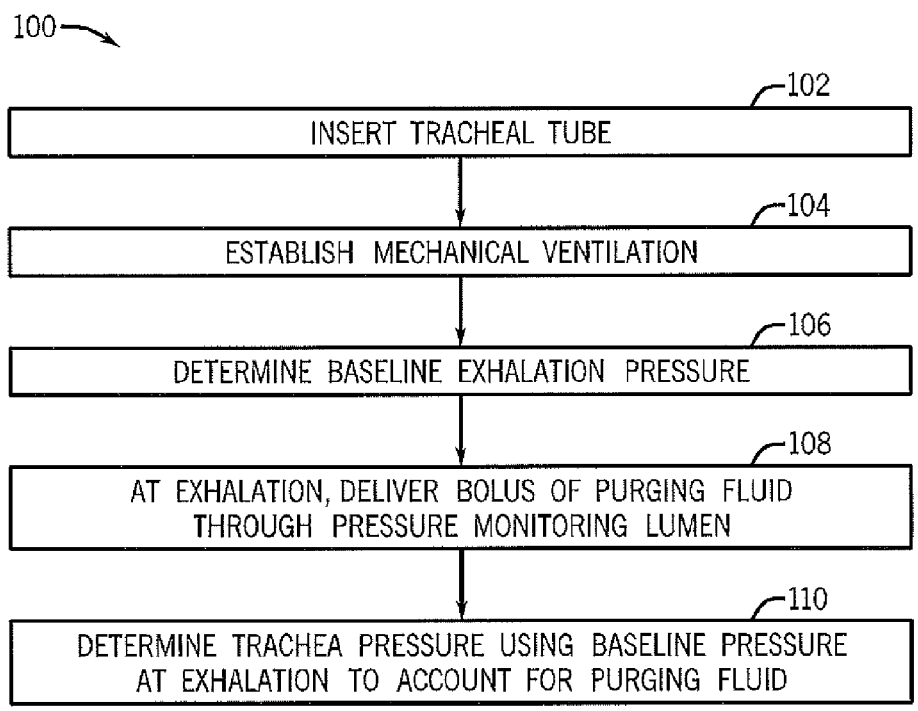
FIG. 5 is a flow diagram of an exemplary method for deriving trachea pressure.

FIG. 5 is an exemplary process flow diagram illustrating a method for determining trachea pressure. The method is generally indicated by reference number 100 and includes various steps or actions represented by blocks. It should be noted that the method 100 may be performed as an automated or semiautomated procedure by a system, such as system 10. Further, certain steps or portions of the method may be performed by separate devices. For example, a portion of the method 100 may be performed by a pressure transducer 36, while another portion of the method 100 may be performed by a monitor 42. In embodiments, the method 100 may be performed continuously or intermittently for long-term patient monitoring or at any appropriate interval depending on the particular situation of the intubated patient.

According to a presently contemplated embodiment, the method 100 begins with the intubation of a patient at step 102. After the patient is intubated and the appropriate respiratory circuit components are put in place, including a tracheal tube 12 as provided herein, mechanical ventilation may be established at step 104. In certain embodiments, a baseline pressure in the lumen 14 may be established at certain points in the breathing cycle to determine which points in a breathing cycle are associated with the lowest baseline pressure at step 106. For example, in a particular embodiment, the pressure at the end of exhalation may represent the lowest pressure in the trachea and, therefore, in the pressure monitoring lumen 14. For other ventilator settings, such as PEEP, the lowest pressure in the trachea may occur at a different point in the breathing cycle. Once the lowest trachea pressure in the context of a breathing cycle has been established, the fluid source 38 may be instructed to deliver a bolus of fluid through the pressure monitoring lumen 14 at step 108 to prevent and/or clear any obstructions that may have formed at opening 16. Pressure transducer 36 may determine the trachea pressure based at least in part on the baseline pressure (step 106) at step 108. For example, the monitor 42 may use the baseline pressure to correct and/or account for the temporary increase in pressure due to the bolus of fluid through the pressure monitoring lumen 14. In this manner, any contribution of the purging pressure in the lumen 14 may be reduced and/or eliminated. In addition, because the bolus may be timed to a particular point in the breathing cycle, the pressure data corresponding to those time points may be tagged for correction.

The pressure measurements from the pressure transducer 36 may be communicated to the monitor 42 for further analysis. The monitor 42 may also receive calibration information from an information element or other storage device associated with the connector 88. It should be noted that the monitor may, of course, receive data or signals directly from the pressure transducer 36. Trachea pressure may be estimated from the pressure in the pressure monitoring lumen and any relevant calibration information.

The relationship between the purging pressure and the pressure in the pressure monitoring lumen may be used to estimate the trachea pressure. For example, a trachea pressure value may be determined by the relationship:

$$P_{TRACHEA} = P_{LUMEN} - P_{PURGING}$$

where the trachea pressure is the pressure in the pressure monitoring lumen 14 after the purging pressure has been subtracted. In one embodiment, the difference between the purging pressure and the airway pressure may be sufficiently low and constant so that the effect on the trachea pressure is within an acceptable error, such as within 5%. In other embodiments, the purging pressure may be subtracted or zeroed out by the monitor 42 to determine the trachea pressure. Depending on the level of purging pressure, the effect on the trachea pressure may be more pronounced at different points along the breathing cycle. Further, the monitor 42 may simply zero out any bolus or other higher pressure fluid delivery by time-stamping instructions for the bolus delivery and disregarding data from particular time periods, by determining the pressure of the bolus and subtracting it out, and/or by substituting the measured pressure during the bolus delivery with the known baseline pressure.

Monitor 42 may use the estimated trachea pressure to determine whether the breathing system 10 is achieving compliance. In certain embodiments, the estimated trachea pressure may be used to correct or adjust settings on a ventilator 40. For example, compliance may be associated with achieving target pressures in the airway during ventilation. If the target pressures in the airway are not achieved, the ventilator settings may be adjusted to increase or decrease the inspiratory pressure. The estimated trachea pressure may be used to determine whether there is a blockage along the tube 12 by calculating the tube resistance using the pressure measurements and flow measurements taken at points closer to the ventilator 40, where a resistance increase may be indicative of a blockage or change in diameter of the tube 12. The monitor 42 may be configured to provide a graphical, visual, or audio representation of the estimated lung pressure. For example, ventilation compliance may be indicated by a green light indicated on a display, while a drop in pressure indicating a blockage in the tube 12 may trigger an alarm, which may include one or more of an audio or visual alarm indication. In one embodiment, the alarm may be triggered if the change in pressure is substantially greater than a predetermined value, substantially less than a predetermined value, or outside of a predetermined range.

Figure 6:
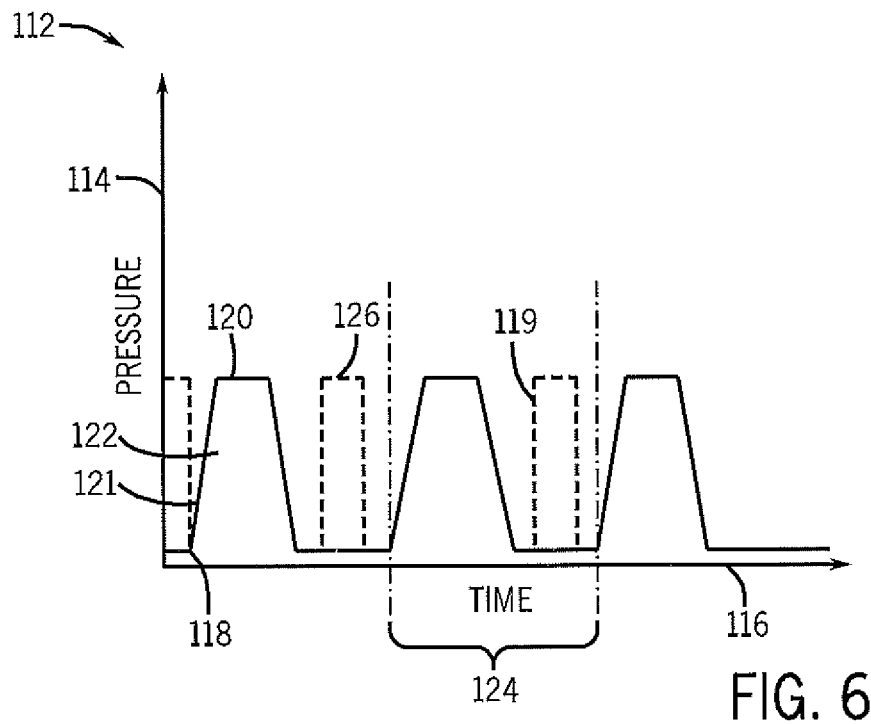
FIG. 6 is a plot of exemplary respiratory pressure and purging pressure applied at a predetermined point during a breathing cycle.

FIG. 6 is a plot 112 that shows an example of a patient respiratory cycle. The pressure 121 delivered by the ventilator 40, as measured by a pressure transducer associated with the ventilator or situated proximally to the patient portion of the respiratory circuit, is plotted on the y-axis 114 against time on the x-axis 116. The airway pressure 121 is cyclical, with a minimum pressure 118, for example at the end of exhalation, followed by a pressure peak 122 with a maximum pressure 120, which may represent inhalation. A single breathing cycle 124 may include both inspiration and exhalation. As shown, the lungs may have a certain baseline minimum pressure 118, which represents the pressure left in the lungs after exhalation. Also shown is an example of a variable purging pressure 119 applied to the pressure monitoring lumen 14 as measured by the pressure transducer 36 associated with the lumen 14. The purging pressure 119 may be applied during a point in the breathing cycle 124 that corresponds most closely to the minimum pressure 118. As shown, a pressure bolus 126 may be applied during exhalation. In particular embodiments, the timing of the pressure bolus 126 may be determined by information from a ventilator 40 (e.g., from an input related to the coded instructions present in the ventilator 40 that trigger the delivery of respiratory gases) or from an airway pressure transducer situated proximally to the patient portion of the respiratory circuit. In other embodiments, the timing of the pressure bolus 126 may be linked to a mechanical feedback from a valve or other respiratory gas delivery mechanism. For example, when a valve in the respiratory circuit switches from an inhalation setting to an exhalation setting, a signal may be provided to the monitor 42. In other embodiments, the bolus 126 may be linked to the pressure transducer in the pressure monitoring lumen 14. When the transducer 36 measures a lower or minimum pressure, the bolus 126 may be delivered.

As shown, the pressure bolus 126 is greater than the minimum pressure 118 and may be, in particular embodiments, less than the maximum pressure 120. In other embodiments, the pressure bolus 126 may be about equal to or greater than the maximum pressure 120. Because the time component of the bolus may be controlled (e.g., through monitor 42), a high-pressure bolus 126 may be used that is sufficiently short in length to minimize the effect on the total pressure in the trachea. Likewise, because the bolus 126 is timed to the minimum pressure 118 portion of the breathing cycle 124, somewhat lower pressure boluses may also be effective at purging the pressure monitoring lumen 14 because the difference between the airway pressure 121 and the purging pressure 119 may be optimized for a lowest possible purging pressure. In addition, the bolus 126 may be applied at every breathing cycle 124, or at intermittent breathing cycles 124.

As shown in FIG. 6, at exhalation, the purging pressure may be greater than the minimum pressure 118. In particular embodiments, during inhalation, the purging pressure may approximately equal to, less than or greater than, the peak pressure 120 delivered by the tube 12. In such embodiments, the ability of the pressure monitoring lumen 14 to be purged may depend on the whether the purging pressure is greater than the trachea pressure. When the purging pressure is greater than the trachea pressure, the gases in the pressure monitoring lumen 14 flow outward into the trachea, applying pressure to any secretions or buildup at the opening 20 or applying sufficient pressure to discourage such buildup. As such, it is contemplated that the purging pressure is generally established at a level greater than the pressure in the lungs for at least one point in the breathing cycle. Further, a purging pressure bolus 126 may result in a rise in vent pressure or lung pressure (not shown), which may depend on the pressure of the bolus 126 and its total volume.

Figure 7:
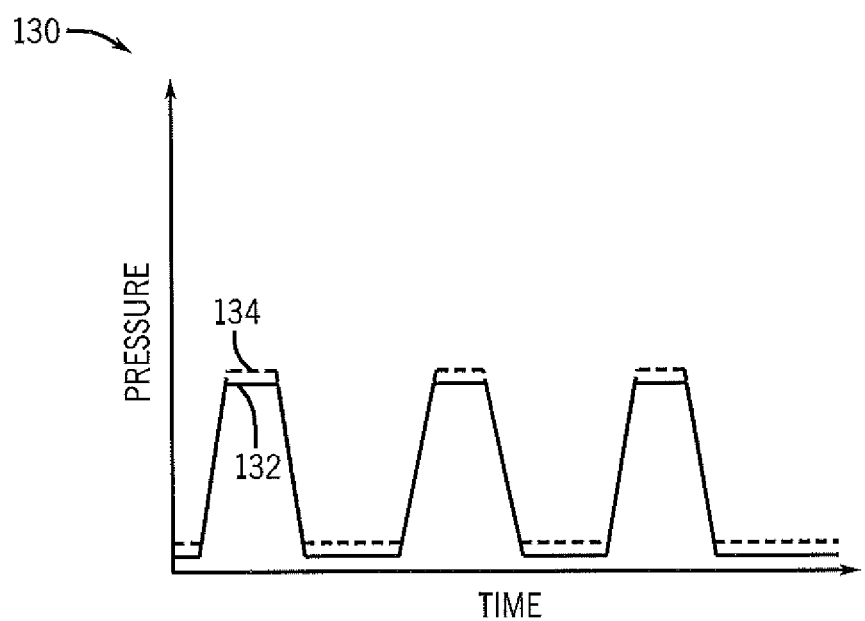
FIG. 7 is a plot of exemplary respiratory pressure and purging pressure over a breathing cycle.

In an alternate embodiment, shown in plot 130 of FIG. 7, the purging pressure 134 may be directed to the pressure monitoring lumen 14 at a substantially constant differential from the airway pressure 132. That is, the difference between the pressure delivered from the ventilator 40 and the pressure from the fluid source 38 may remain about the same over the course of the breathing cycle. In such embodiments, the purging pressure may have a constant correction factor and the monitor 42 may be able to simply subtract the differential from the measured pressure to determine a corrected trachea pressure. In the embodiment shown, because the purging pressure 134 in the lumen 14 is greater than the ventilator pressure 132, purging may occur during the entire breathing cycle. It should be noted that the purging pressure 134 may be applied during every breathing cycle or during intermittent breathing cycles. Further, the differential may be calculated from information from the ventilator settings, from the pressure transducer 36, and/or from a pressure transducer in the airway proximal to the patient portion of the respiratory circuit. As shown, the constant differential may be substantially synchronized with the patient's breathing cycle or, in other embodiments, may operate on a slight delay, depending on any time delay involved in providing feedback to the fluid source 38.

Figure 8:
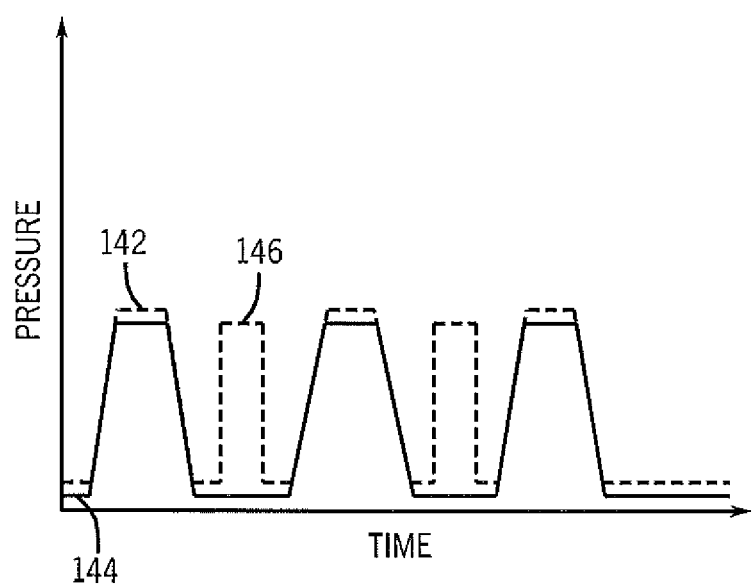
FIG. 8 is a plot of exemplary respiratory pressure and a purging pressure bolus applied at a predetermined point during a breathing cycle in addition to a bolus applied intermittently.

FIG. 8 is a plot 140 of a presently contemplated embodiment in which the purging pressure 142 may be a substantially constant differential from the airway pressure 144 with the exception of occasional boluses 146 of purging pressure that are timed to coincide with certain portions of a breathing cycle. In the depicted embodiment, the boluses 146 are timed to coincide with minimum pressure points in the breathing cycle. The boluses 146 may occur regularly or intermittently, or may occur only in response to certain events, such as blockages in the pressure monitoring lumen 14.

Figure 9:
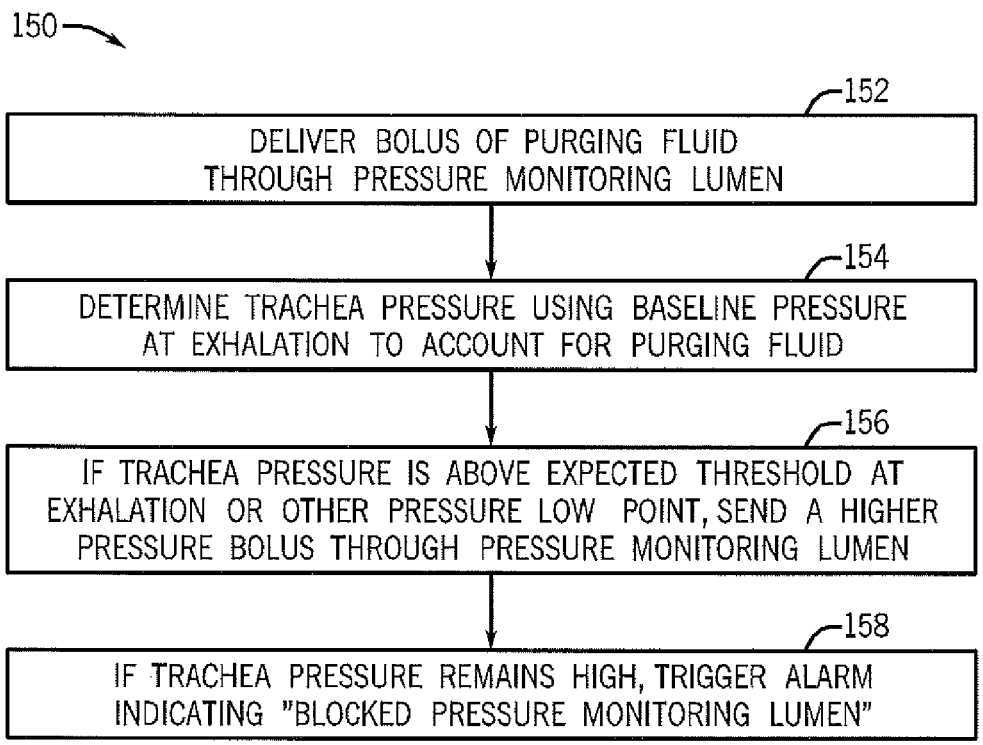
FIG. 9 is a flow diagram of an exemplary method for determining if a pressure monitoring lumen is blocked.

Such blockages in the pressure monitoring lumen 14 may be detected using measured trachea pressure information along with known (or estimated) resistance information for the lumen 14. During normal operation of the tube 12 and lumen 14, the pressure measured by the lumen 14 may follow certain anticipated characteristics based on the ventilator settings and the purging pressure settings. When the measured pressure deviates from such settings, e.g., the measured pressure does not follow a cyclical pattern but instead continues to rise even during exhalation, a blockage may be present in the lumen 14 that prevents the fluid in the lumen 14 from flowing out into the tracheal space 28. According to a particular embodiment depicted in FIG. 9, a method 150 for assessing lumen blockage begins with the normal operation of the purging components in conjunction with an intubated patient.

Figure 10:
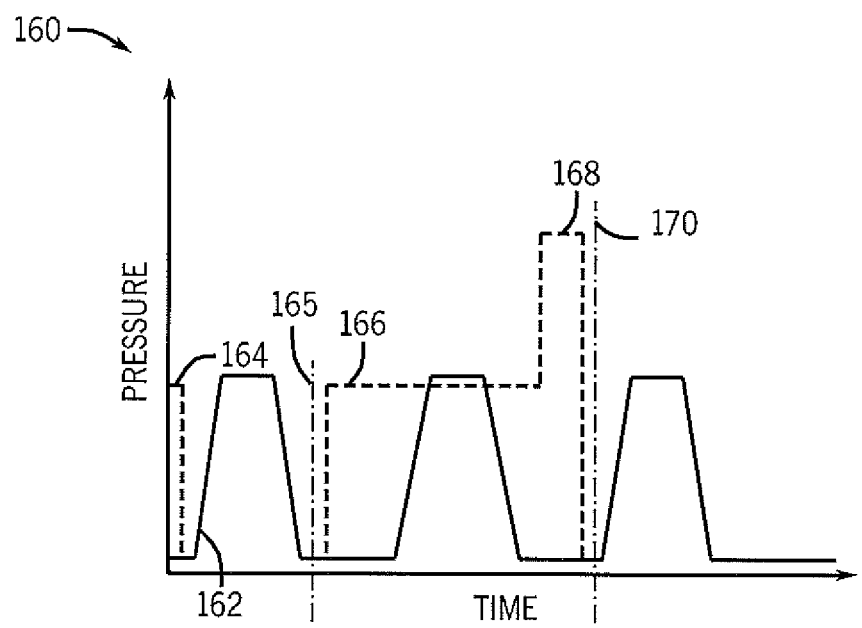
FIG. 10 is a plot of exemplary respiratory pressure and a purging pressure bolus for a pressure monitoring lumen with a blockage.

For example, an occasional purging bolus 166 may be delivered through the lumen 14 (or, in other embodiments, a steady purging flow may be delivered) at step 152, as shown by plot 160 FIG. 10. The trachea pressure is measured by the associated pressure transducer 36 and may be corrected by using an established baseline pressure to account for the purging pressure. If the measured trachea pressure (or the corrected trachea pressure) is above an established threshold or otherwise deviates from an expected pattern, particularly when the measured pressure is high at an expected "quiet" time in respiration (i.e., a respiratory pressure low point), a high-pressure bolus 168 may be delivered through the pressure monitoring lumen 14 in an attempt to clear a potential blockage at step 156. As shown in FIG. 10, the deviation from expected pressure may be triggered by an event 165, which may represent the blockage of opening 20 by mucus or other secretions. After the normal bolus 166 is delivered, the blockage may prevent the fluid from leaving the lumen 14, resulting in a sustained higher pressure. When such deviation is detected by the pressure transducer 36 and communicated to a coupled device (e.g., monitor 42), the high pressure bolus 168 may be triggered. The high-pressure bolus 168 may be substantially higher than the initial bolus 166. For example, the high-pressure bolus may be at least twice the peak respiration pressure or at least 60 cm $H_2O$. The high pressure bolus 168 may clear the blockage at event 170. If so, the pressure in the lumen 14 will drop and the measured pressure will return to expected levels. If, even after delivery of a high-pressure bolus 168, the measured pressure remains high, an alarm or other indication may be provided on the monitor 42 indicating that the lumen 14 is blocked.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of tracheal tube pressure, but these techniques may also be utilized for the measurement and/or analysis of the cuff pressure for any medical device inserted into a patient's airway. Rather, the various embodiments may cover all modifications, equivalents, and alternatives falling within the spirit and scope of the disclosure as defined by the following appended claims.

What is claimed is:

1. A method comprising:
measuring a tracheal pressure of a patient's trachea with a pressure transducer in fluid communication with a pressure monitoring lumen, wherein the pressure monitoring lumen is associated with a tracheal tube;
receiving information related to a respiratory gas pressure over a breathing cycle of a patient;
determining a baseline pressure associated with a minimum pressure point over the course of the breathing cycle of the patient;
delivering a purging fluid as a bolus of purging fluid timed to coincide with the minimum pressure point over the course of the breathing cycle of the patient through the pressure monitoring lumen at a purging pressure greater than the respiratory gas pressure; and
determining a corrected tracheal pressure of the patient's trachea that accounts for the bolus of purging fluid based at least in part on the baseline pressure, wherein determining the corrected tracheal pressure comprises substituting the measured pressure during the bolus delivery with the baseline pressure.

2. The method of claim 1, further comprising determining a second corrected tracheal pressure at a different point over the course of the breathing cycle based on a difference between a purging pressure and the tracheal pressure of the patient's trachea.

3. The method of claim 1, comprising determining the baseline pressure in the pressure monitoring lumen at exhalation and using the baseline pressure to determine the corrected tracheal pressure.

4. The method of claim 3, wherein the baseline pressure is a pressure left in the lungs after an end of exhalation.

5. The method of claim 1, wherein delivering the purging fluid is controlled by instructions encoded within a processor.

6. The method of claim 1, further comprising determining a second corrected tracheal pressure at a different point over the course of the breathing cycle by subtracting a purging pressure from the pressure in the pressure monitoring lumen.

* * * * *